United States Patent
Fan et al.

(10) Patent No.: US 10,405,565 B2
(45) Date of Patent: Sep. 10, 2019

(54) PICHIA KLUYVERI STRAIN AND ITS APPLICATION IN PRODUCING NONALCOHOLIC RED BAYBERRY JUICE

(71) Applicants: Liuping Fan, Wuxi (CN); Jing Du, Wuxi (CN); Jieying Li, Wuxi (CN)

(72) Inventors: Liuping Fan, Wuxi (CN); Jing Du, Wuxi (CN); Jieying Li, Wuxi (CN)

(73) Assignee: Jiangnan University, Wuxi, JS (CN)

( * ) Notice: Subject to any disclaimer, the term of this patent is extended or adjusted under 35 U.S.C. 154(b) by 84 days.

(21) Appl. No.: 15/236,393

(22) Filed: Aug. 13, 2016

(65) Prior Publication Data
US 2017/0258113 A1    Sep. 14, 2017

(30) Foreign Application Priority Data
Mar. 10, 2016 (CN) .......................... 2016 1 0137565

(51) Int. Cl.
| | | |
|---|---|---|
| *A23L 2/72* | (2006.01) | |
| *A23L 2/38* | (2006.01) | |
| *A23L 2/02* | (2006.01) | |
| *C12R 1/84* | (2006.01) | |
| *A23L 2/46* | (2006.01) | |
| *A23L 2/60* | (2006.01) | |

(52) U.S. Cl.
CPC .............. *A23L 2/382* (2013.01); *A23L 2/02* (2013.01); *A23L 2/46* (2013.01); *A23L 2/60* (2013.01); *A23L 2/72* (2013.01); *C12R 1/84* (2013.01); *A23V 2002/00* (2013.01)

(58) Field of Classification Search
CPC ... A23L 2/382; A23L 2/02; A23L 2/72; A23L 2/46; A23L 2/60
USPC ................................................... 426/51
See application file for complete search history.

(56) References Cited

U.S. PATENT DOCUMENTS

| | | | | |
|---|---|---|---|---|
| 4,999,209 A | * | 3/1991 | Gnekow | C12G 3/085 426/330.4 |
| 2010/0159069 A1 | * | 6/2010 | Chelle | C12G 1/0203 426/13 |
| 2013/0045301 A1 | * | 2/2013 | Swiegers | A23L 2/02 426/15 |
| 2016/0130540 A1 | * | 5/2016 | Malcorps | C12G 3/02 426/16 |

OTHER PUBLICATIONS

Guoxiang, L. et al. 2004. Development of low alcohol red bayberry wine. English Abstract. (Year: 2004).*
Fai, A. E. C. et al. 2014. Biocat. Agric. Biotechnol. 3:343-350 (Year: 2014).*
Erten, H. et al. J. Ins. Brewing. 2001. 107: 207-215 (Year: 2001).*

* cited by examiner

*Primary Examiner* — Hamid R Badr
(74) *Attorney, Agent, or Firm* — Lili Chen

(57) ABSTRACT

The present invention provides a novel *Pichia kluyveri* strain (CCTCC NO: M 2015626) and the method of using this new strain to produce fermented nonalcoholic red bayberry juice. The method comprises incubating *Pichia kluyveri* CCTCC NO: M 2015626 with red bayberry juice in a fermentation process to make the fermented nonalcoholic juice, which includes an aerobic, anaerobic and a low temperature fermentation. The fermented bayberry juice of the present invention has bright color, low alcohol content (<0.5%) and high nutritional values. It maintains the characteristic fruity flavor of red bayberries with added mellow taste and aroma from the fermentation.

10 Claims, No Drawings

Specification includes a Sequence Listing.

PICHIA KLUYVERI STRAIN AND ITS APPLICATION IN PRODUCING NONALCOHOLIC RED BAYBERRY JUICE

CROSS-REFERENCES AND RELATED APPLICATIONS

This application claims the benefit of priority to Chinese Application No. 201610137565.3, entitled "A novel *Pichia kluyveri* strain and its application in producing nonalcoholic red bayberry juice", filed Mar. 10, 2016, which is herein incorporated by reference in its entirety.

BACKGROUND OF THE INVENTION

Field of the Invention

The present invention relates to the field of microbial fermentation. In particular, it relates to a novel *Pichia kluyveri* strain and its application in producing fermented nonalcoholic red bayberry juice.

Description of the Related Art

Red bayberry (Yangmei in Chinese) is an indigenous fruit of China that has bright color and rich flavor. Over 90% of its spherical fruit is edible. Red bayberry is rich in sugar, organic acids and vitamins, and also contains anthocyanins, polyphenols and minerals such as calcium, phosphorus, iron, and potassium. It is a very popular fruit with high nutritional and medical value. It is mainly consumed as a fresh fruit. However, since the fruit is ripe in rainy seasons, short shelf life and limited distribution often leads to large amounts of fruits becoming rotten and wasted. Therefore, there is an urgent need of developing methods for making products from fresh red bayberry fruits. Red bayberry products in the market mainly include red bayberry juice, red bayberry wine, red bayberry fruit can, and preserved bayberry fruit, which hardly meets consumers' pursuit of bayberry products with fresh fruit taste.

At present, consumers become increasingly interested in fermented fruit beverages having rich fermented flavors and fresh fruit taste. Nonalcoholic fermented juice, which contains low alcohol content (<0.5%) and preserves most of fruit's nutrition, color and flavor, is suitable for all types of consumers including women, elderly people, drivers and children. Development of nonalcoholic fermented fruit juice are still in its early stage. The method for making fermented nonalcoholic red bayberry juice has not been reported.

Commonly available yeasts on the market are wine-preparing yeasts and brewing yeasts. Fermentation pH for these yeasts is around 3.5 and the optimum fermentation pH for them is above 4. The pH of red bayberry juice is around 3, and even small adjustment of fermentation pH can significantly affect the juice taste and quality. Increasing the fermentation pH to 3.5 makes anthocyanin unstable, which results in a large loss of anthocyanin and serious color fading in the final product. It is not desirable to adjust pH during red bayberry fermentation. On the other hand, most commercial yeasts are inhibited at fermentation pH 3.0 and the aroma production ability is also greatly reduced at this pH. Nonalcoholic beverage fermentation is usually performed under low temperature (10-20° C.), which helps to control the fermentation speed and allows accumulation of rich flavors. Fermentation under lower temperature leads to longer fermentation time and larger energy consumption. Physical techniques (distillation, reverse osmosis, etc.) are used for reducing the content of alcohol to less than 0.5%, which requires large equipment investment and energy consumption. There is a need to develop cost effective methods for making high quality nonalcoholic red bayberry fermented juice.

DETAILED DESCRIPTION

The first goal of the present invention is to provide a novel *Pichia kluyveri* XT110 strain that is suitable for making fermented nonalcoholic red bayberry juice. On Oct. 20, 2015, *Pichia kluyveri* XT110 was conserved in China Center for Type Culture Collection (CCTCC) located at Wuhan University, China, with code CCTCC NO: M 2015626.

Observed under a microscope, *Pichia kluyveri* XT110 is gemmiparous, and has an elliptical shape with a size of (3.0-4.5) μm×(6.0-8.5) μm. The colony of *Pichia kluyveri* XT110 is white in color and 3.2-4.2 mm in diameter. It has a convex body, a dry and wrinkled surface and an irregular edge, and it sends out fruity smells.

The *Pichia kluyveri* produces sufficient gas to fill the Durham tube within 24 hrs when incubated under 20-30° C. in a culture medium of pH 2.5, or in a sterilized red bayberry juice medium containing 30% sugar.

The *Pichia kluyveri* reaches the end of log phase after incubated in a culture medium at pH 5.0, 28° C. for 9 hrs, with the cell mass of $2\times10^8$ CFU/mL, which is suitable for inoculation.

The second goal of the present invention is to provide a novel method for producing nonalcoholic red bayberry juice by use of *Pichia kluyveri*, which makes up the gap in the nonalcoholic red bayberry juice market and overcomes the shortcomings of the existing processing technologies. Nonalcoholic red bayberry juice made by the present invention possesses a bright color, high content of anthocyanin, low content of alcohol (<0.5%), rich fruity taste and balanced flavor.

The method comprises the following steps:

(1) Material pretreatment: red bayberry fruits are washed, deseeded, squeezed; the resulting supernatant juice and residue are sterilized and cooled to room temperature;

(2) Seed culture preparation: The *Pichia kluyveri* CCTCC NO: M 2015626 is activated to prepare a seed culture;

(3) Primary fermentation: *Pichia kluyveri* cells are harvested from the seed culture, washed and inoculated into the sterilized red bayberry juice, incubated aerobically at 15-35° C. for 1-10 hrs, and then incubated anaerobically until a fermentor weight loss achieves 1.0-2.8 g/L; and the culture broth is filtered to remove residues.

(4) Secondary fermentation: the filtered culture broth is incubated at 4-8° C. for 20-30 days. Sugar content and acidity of the juice is adjusted for the best taste, and the cultured juice is sterilized to obtain a final product.

In one embodiment, ripe, undecayed and deep colored red bayberries are chosen as the raw material to make the red bayberry nonalcoholic juice.

In one embodiment, the squeezed red bayberry juice and residue are sterilized under 100° C. for 5 min and then cooled immediately to room temperature in step (1).

In one embodiment, *Pichia kluyveri* CCTCC NO: M 2015626 is incubated in the YPD medium for a three-stage activation process in the step (2).

In one embodiment, the three-stage activation process in the step (2) comprises the following steps: a single colony of *Pichia kluyveri* CCTCC NO: M 2015626 is picked and transferred to a new YPD agar medium, incubated at 28° C. for 24 hrs (stage 1); 3 colonies are scraped off using an inoculating loop, inoculated into 50 mL YPD medium (pH 5.0), and incubated at 28° C., 150 rpm for 12 hrs (stage 2); The yeast cells are then transferred to 100 mL YPD medium (pH 5.0) at an volume ratio of 10% (v/v), and incubated at 28° C., 150 rpm for 9 hrs (stage 3); and the resulting cells are diluted to $2\times10^8$ cfu/mL using sterile water.

In one embodiment, the volume of the added bayberry juice is 50% of that of the fermentor, the amount of added red bayberry residue is 20-140 g/L in the step (3).

In one embodiment, the amount of added red bayberry residue is 80 g/L in the step (3).

In one embodiment, the step (3) is carried out as follows: culture broth of *Pichia kluyveri* CCTCC NO: M 2015626 is centrifuged, cell precipitation is harvested and transferred at an inoculation rate 5% (v/v) to the sterilized red bayberry juice; and *Pichia kluyveri* cells are cultured in the red bayberry juice aerobically at 15-35° C. for 1-10 hrs and then incubated anaerobically until achieving a weight loss of 1.0-2.8 g/L; and the culture broth is filtered to remove residues.

In one embodiment, step (3) is carried out at 28° C. for 4 hrs for aerobic fermentation; the anaerobic fermentation performed until achieving a weight loss of 2.3±0.2 g/L.

In one embodiment, step (4) is carried out through transferring the filtered culture broth into a sterile container, incubating at 4-8° C. for 20-30 days, adjusting the sugar content and acidity to the best taste, and pasteurizing the culture broth to obtain the final product.

The advantage of the present invention includes:

1. The *Pichia kluyveri* CCTCC NO: M 2015626 is very suitable for nonalcoholic red bayberry fermentation, which is capable of being fermented under the pH (2.5-3.0) of red bayberry juice without adjusting the pH or adding extra sugar, thus greatly simplifying the fermentation process. Commercial Angel wine yeast RV818 is hardly fermented under the same condition. Before optimization of the fermentation process, anthocyanin content in fermented juice produced by *Pichia kluyveri* CCTCC NO: M 2015626 is 106 mg/L, which is 103.2% higher than that produced by commercial Angel wine yeast. The bayberry juice of the present invention is rich in fruity and mellow aroma and has a characteristic flavor of red bayberries, while juice fermented by commercial Angel wine yeast lacks fruity aroma and has an obvious alcoholic smell. The juice produced by the present invention has pure and fruity taste of red bayberries with a pleasant aftertaste, whereas the juice made by Angel wine yeast has a relatively plain taste. Results of sensory evaluation show that the present juice has a score that is 25.9 higher than that of the juice made by commercial Angel wine yeast RV818. *Pichia kluyveri* is a yeast strain very suitable for red bayberry juice fermentation.

2. Process of nonalcoholic juice fermentation is usually performed under low temperatures in order to limit the generation of alcohol during the fermentation, which leads to a long fermentation period for over 20 days. The present invention provides a fermentation method at 28° C. for less than 24 hours, which greatly reduces the fermentation time and saves the energy costs.

3. Most fruit wines are generally fermented under anaerobic conditions, which results in high alcohol concentration and less aroma or taste in the final products. The present invention provides a fermentation process with an aerobic and an anaerobic fermentation phase. The 4-hour aerobic fermentation not only promotes yeast cell growth, but also improves the product flavor, and at the same time, it prevents ester oxygenation caused by long time aerobic fermentation. The control of the anaerobic fermentation is based on the fermentor weight loss, which is a measure of $CO_2$ generated during the fermentation. It is found that the weight loss of 2.3±0.2 g/L is a good stopping point that can limit the alcohol content in the products to be less than 0.5%.

4. Fermentations of red bayberry are usually performed with bayberry juice instead of whole fruits because solid fruit residues can absorb large amounts of juice during the fermentation, which reduces the contacting surface areas between yeasts and the juice, and prevents effective fermentation. Fermentation using supernatant bayberry juice, however, has the disadvantage of easy decomposition of anthocyanin and color-fading. By controlling the amount of fruit residues added in the fermentation, the present invention can produce a fermented juice with a bright color and a rich bayberry flavor while limiting the impeding effect of red bayberry residues.

Deposit of Biological Materials

A *Pichia kluyveri* XT110 strain was deposited on Oct. 20, 2015, at China Center for Type Culture Collection (Wuhan University, Wuhan, Hubei, China), an International Depositary Authority (IDA) as established under the Budapest Treaty on the International Recognition of the Deposit of Micro-organisms for the Purposes of Patent Procedure. The accession number of *Pichia kluyveri* XT110 is CCTCC NO: M 2015626.

EXAMPLES

Example 1. Strain Isolation of Yeast Strains Suitable for Using in Red Bayberry Fermentation (1) Isolation of yeast strains: Soil in Wuxi red bayberry orchard was collected, mixed with 100 mL sterile physiological saline, and vortexed for 10 min; 1 mL supernatant of the vortexed solution was transferred to 30 mL YPD medium (pH 5.0), and incubated at 28° C., 150 r/min for 24 hrs; 1 mL culture broth was gradient diluted for 10 times and spread on YPD agar plates, incubated at 28° C. for 24 hrs. 25 strains with characteristic morphologies of yeasts were selected and conserved on YPD agar slants.

(2) Activation of yeasts: 3 rings of each colony were scraped off using an inoculation loop and inoculated into 50 mL YPD medium (pH 5.0), and incubated at 28° C., 150 rpm for 12 hrs; cell concentration of culture broth were adjusted to $2\times10^8$ cfu/mL using physiological saline.

(3) Preparation of fermentation medium: ripe, undecayed, deep-colored red bayberries were washed, deseeded, squeezed and filtered using gauzes; and were sterilized at 100° C. for 5 min and cooled immediately to room temperature. The sterilized bayberry broth was used as the bayberry fermentation medium below.

(4) Screening of yeasts suitable for bayberry fermentation:

Preliminary screening (the Durham tube method): the activated yeasts were inoculated at 10% (v/v) to 10 mL bayberry fermentation medium (with a Durham tube), and incubated at 24° C. for 48 hours. The gas production was monitored every 12 hours. The color and smell of culture broth were detected after the fermentation was finished. Four strains that produce culture broths with bright colors and aromatic smells, and produce gas to fill of the Duham tube within 24 hrs of fermentation were isolated.

Secondary screening (fermentation in triangular flasks): the activated yeasts were inoculated at 5% (v/v) to the bayberry fermentation medium, and incubated at 24° C. in triangular flasks equipped with fermentation bung. The bottle was shaken every 2 hrs until the weight loss reached 2.3±0.2 g/L and the fermentation was stopped (it is confirmed in preliminary experiments that the alcohol content of the culture raised to 0.5% when the weight loss of the fermentation increased to 2.8 g/L). Total acid, residual sugar, and contents of anthocyanin and alcohol in the culture broth were determined after the fermentation. Sensory indexes including color, smell, flavor and taste of the culture broth were evaluated. The juice fermented by commercial active dry yeast (Angel Yeast Co., Hubei, China) RV171 and BV818 were used as controls. The sensory evaluation criteria were listed in table 1. Physical and chemical indexes of red bayberry juices were shown in table 2.

TABLE 1

Sensory evaluation criteria of nonalcoholic red bayberry juice

| Color (30) | Smell (30) | Flavor (20) | Taste (20) |
| --- | --- | --- | --- |
| purplish red and sufficient gloss (21-30) | Bayberry smell, mellow and fruity (21-30) | Bayberry smell, with appropriate amount of sourness and sweetness, No acerbity or peculiar taste (14-20) | Pure, mellow and aromatic taste, rich aftertastes (14-20) |
| Deep red or deep purple, Insufficient gloss (11-20) | Insufficient bayberry smell, alcoholic and slight fruity (11-20) | Bayberry smell, with inappropriate amount of sourness and sweetness, acerbic taste (7-13) | thin taste, insufficient aroma, lack of aftertastes (7-13) |
| Light red, seriously faded color, lackluster (<10) | No bayberry smell, or with unpleasant smell (<10) | No bayberry smell, with inappropriate amount of sourness and sweetness, with unpleasant taste (<6) | Unpleasant tastes (<6) |

TABLE 2

Physical and chemical indexes in nonalcoholic juice fermented by different strains

| | Strain | | | | | |
| --- | --- | --- | --- | --- | --- | --- |
| Index | XT97 | XT103 | XT110 | XT112 | RV171 | BV818 |
| Alcohol (%) | 0.4a | 0.4a | 0.4a | 0.4a | 0.4a | 0.1b |
| Anthocyanin (mg/L) | 101c | 117a | 106b | 94d | 52f | 193e |
| Residual sugar(g/L) | 23a | 23a | 23a | 22a | 22a | 83b |
| Total acid (g/L) | 8.74d | 8.46a | 8.54b | 8.95e | 8.71d | 8.64c |
| Sensory score | 73.8b | 71.5c | 78.6a | 63.3d | 48.5f | 52.7e |

As shown in table 2, alcohol contents in nonalcoholic juices fermented by the first five yeast strains were 0.4% (less than 0.5%), conforming to the constituent requirements of the legal provisions for nonalcoholic beverages. Contents of anthocyanin were significantly different ($p<0.05$) among juices made by different methods. Strain XT103 is the best performer that produces 117 mg/L authocyanin in fermented juice, and XT110 took the second place with production of authocyanin of 106 mg/L, while RV171 is the worst with authocyanin production of only 52 mg/L. Residual sugar of juice from different fermentation appeared little difference ($p<0.05$), which were between 22-23 g/L. Total acid in the juices differed significantly from each other ($p<0.05$). Juice fermented by XT103 possessed the minimum total acid, while XT112 had the maximum value. The sensory scores of the juices showed significant differences as well ($p<0.05$). Strain XT110 has the highest sensory score of 78.6 and strain XT97 has the second highest one of 73.8. The worst performer of all is commercial Angel wine yeast BV818, which produces a juice with 0.1% alcohol content, 83 g/L residual sugar (9.7% sugar reduction), and a sensory score of 52.7. There is little weight loss during the fermentation using wine yeast BV818, indicating that it does not perform effective fermentation under this culture condition.

According to the sensory evaluation criteria in table 1, the first 3 strains (XT97, XT103 and XT110) showed little difference on the color of resulting juices, XT112 and RV717 produced juices with a light reddish color, and BV818 presented a juice with a deep red color, similar to the color of red bayberries. In terms of the smell, XT97 and XT110 produced a bayberry juice with an aromatic fruity smell, characteristic of bayberry flavor. XT103 produced a juice with a light aroma and a little acid taste. XT112, RV171 and BV818 had worse scores in smell. In terms of the flavor, all the 6 strains produced juices with strong red bayberry taste. The juice made by XT110 has no obvious acid taste, while juices made by other strains have obvious acid taste which may come from the organic acids in the juices. In terms of the taste, juices made by the first three stains (XT97, XT103 and XT110) have pure and mellow taste, whereas the taste of juices made by XT112, RV171 and BV110 is relatively plain and thin. In addition, juice made by XT110 has a very pleasant aftertaste. In summary, the juice made by XT110 (later named as *Pichia kluyveri* CCTCC NO: M 2015626) has the best overall sensory evaluation score and is chosen as the best strain for red bayberry juice fermentation.

(5) Morphology observation: XT110 selected from the previous procedure was inoculated to a YPD medium, incubated at 28° C. for 2 days. The immersion method was used to observe the morphology and budding condition of the XT110 cells under a microscope. An ocular micrometer was used to measure the size of the cells. The cells are elliptical, gemmiparous and have a size of (3.0-4.5) μm×(6.0-8.5) μm under the microscope. The colony is 3.2-4.2 mm in diameter, white in color, dry and wrinkled on the surface, irregular on the edge, has bumps in the middle and sends out a fruity smell.

(6) Molecular biological assay: Genome DNA of the strain was extracted and sequenced in Shanghai Bioengineering Company. The sequencing result showed that the strain was classified to be a *Pichia kluyveri*, having the sequence of 26S rDNA D1/D2 region as follows:

```
GAGGAAAAGGAAACCAACAGGGATTGCCTCAGTAGCGGCGAGTGAAG

CGGCAAGAGCTCAGATTTGAAATCTCACCTAGTGTGCGAGTTGTAAATTG

CAGGTTGGAGTCTCGGGTTAGACGTGTGTGCAAGTCCCTTGGAACAGGGT

GCCACTGAGGGTGAGAGCCCCGTAGCGTGCATGTCGACACCTGTGAGGCC

CTTCTGACGAGTCGAGTTGTTTGGGAATGCAGCTCTAAGTGGGTGGTAAA

TTCCATCTAAGGCTAAATATTGGCGAGAGACCGATAGCGAACAAGTACTG

TGAAGGAAAGATGAAAAGCACTTTGAAAAGAGAGTGAAACAGCACGTGAA

ATTGTTGAAAGGGAAGGGTATTGGGCTCGACATGGGATTTACGCATCGTT

GCCTCTCGTGGGCGGCGCTCTGGGTTTTTCCTGGGCCAGCATCGGTTTTC

GTTGCAGGATAAGGACAATTGGAATGTGGCTCCTCGGAGTGTTATAGCCT

TTTGTAGATGCTGCGTATGGGGACCGAGGGCTGCGGCGGACTCGTTTCGT

CTCGGATGCTGGCACAACGGCGCAATACCGC
```

(7) Analysis of the tolerance of XT110 strain: The Durham tube was used to analyze the environmental tolerance of the strain. *P. kluyveri* XT110 was activated, inoculated to a standard YPD medium and incubated under various temperatures (10° C., 15° C., 20° C., 25° C., 30° C., or 35° C.). Activated XT110 cells were inoculated to YPD media with various sugar concentrations (20%, 30%, 40%, or 50%), or inoculated to YPD media at various pHs (1.5, 2.0, 2.5, or 3.0), and then incubated at 28° C. for 96 hrs. The speed of gas production were monitored every 24 hrs. The results showed that *Pichia kluyveri* produced sufficient gas to fill the Durham tube within 24 hrs when incubated under 20-35° C., in a medium with pH 2.5, or in a medium with 30% sugar.

(8) Measurement of cell growth curve: Colonies of *Pichia kluyveri* were picked, inoculated to new YPD agar plates, and incubated at 28° C. for 24 hrs. 3 rings of colonies were scraped off using an inoculating loop and inoculated into a YPD medium, incubated at 28° C., 150 rpm for 12 hrs, and then inoculated at 10% volume ratio to 100 mL YPD medium. Cell growth (OD) after a 12-hr incubation was determined under different incubation temperatures (22° C., 24° C., 26° C., 28° C., 30° C., 32° C. and 34° C.), and at different pHs (3.0, 3.5, 4.0, 4.5, 5.0, 5.5, 6.0, 6.5 and 7.0), and the cell growth curve was measured to determine the optimum condition. The results showed that the optimum temperature for this strain is 28° C., and the optimum pH of the medium is 5.0. The strain reached the final stage of growth after 9 hours of incubation, and cell mass achieved $2 \times 10^8$ cfu/mL under the optimum culture condition.

Example 2. Optimization of Nonalcoholic Red Bayberry Juice Fermentation Process Using *Pichia kluyveri* CCTCC NO: M 2015626

(1) Material pretreatment: ripe, undecayed, deep-colored red bayberries were chosen as the starting material. The red bayberries were washed, deseeded, squeezed and filtered using gauzes. The resulting juice was transferred to a fermentation flask, filling half of the flask. Different amounts of the bayberry residues were added to the fermentation flask. The bayberry juice and residues were sterilized at 100° C. for 5 min and cooled immediately to room temperature;

(2) Seed culture preparation: A single colony of *Pichia kluyveri* CCTCC NO: M 2015626 was picked, inoculated to a new YPD agar plate, and incubated at 28° C. for 24 hrs. Three rings of the resulting colonies were scraped off using an inoculating loop, inoculated into 50 mL YPD medium (pH 5.0), and incubated at 28° C., 150 rpm for 12 hrs. The culture broth was then transferred at an inoculation ratio of 10% (v/v) into 100 mL YPD medium (pH 5.0), incubated at the same condition for 12 hrs. Sterile water was added to adjusting the cell concentration to $2 \times 10^8$ cfu/mL;

(3) Primary fermentation: *Pichia kluyveri* XT110 cells precipitation were harvested after centrifugation of culture broth at 5000 r/min for 5 min. The XT110 cells were washed and inoculated into the sterilized red bayberry juice, aerobically incubated in the fermentation flask covered with a gauze for a certain time (e.g. at 15-35° C. for 1-10 hours). The gauze was then replaced with a sterile fermentation bung and the fermentation was performed under anaerobic condition at the same temperature until reaching a weight loss of 1.0-2.8 g/L.

(4) Secondary fermentation: the culture broth above was filtered and transferred into a sterile container (filling up to 95% of its volume), and incubated at 4-8° C. for 20-30 days to obtain a raw juice. The sugar content and acidity of the raw juice was manually adjusted to achieve the best taste. The adjusted juice was subsequently sterilized to obtain the final product.

(5) The effect of fermentation conditions on the quality of the bayberry juice

When the fermentation temperature is below 20° C., generation of aroma is very slow or not obvious. It is hard to control the fermentation speed at a temperature above 28° C., which causes a loss of aromatic compounds with the fast evaporation of $CO_2$. When fermented in filtered red bayberry juice only, large amounts of anthocyanin were destroyed during the fermentation, leading to nutritional loss and faded color. Adding appropriate amount of bayberry residues into the fermentation broth can increase the anthocyanin content and improve the juice flavor. 20 grams of residues per 100 mL red bayberry juice were generated during the pretreatment. Addition of more than 80 g/L fruit residue to the fermentation broth can negatively impact the effectiveness of the fermentation. At the initial stage of the fermentation, aerobic fermentation can greatly increase the growth rate of the yeast and improve its ability to produce aromatic compounds. However, aerobic incubation overtime can lead to a peculiar taste in the final product.

The optimum fermentation condition is: incubation temperature at 28° C., addition of 80 g/L bayberry residue and aerobic fermentation for 4 hours. The sensory indexes of the red bayberry juice produced under the optimum condition is shown in table 3.

TABLE 3

| | Indexes of nonalcoholic red bayberry juice produced under the optimum fermentation condition | | | | |
|---|---|---|---|---|---|
| Index | Alcohol strength (%) | Anthocyanin (mg/L) | Residual sugar (g/L) | Total acid (g/L) | Sensory score (100) |
| Result | 0.4 | 153 | 23 | 8.52 | 91.7 |

While the present invention has been described in some detail for purposes of clarity and understanding, one skilled in the art will appreciate that various changes in form and detail can be made without departing from the true scope of the invention. All figures, tables, appendices, patents, patent applications and publications, referred to above, are hereby incorporated by reference.

What is claimed is:

1. A method for producing a fermented nonalcoholic red bayberry beverage, comprising incubating *Pichia kluyveri* XT110 and a red bayberry juice in an aerobic fermentation process at 15-35° C. for 1-10 hours followed by an anaerobic fermentation of the same fermentation medium until achieving a weight loss of 1.0-2.8 g/L fermentation medium, wherein said fermented nonalcoholic red bayberry beverage has less than 0.5% alcohol by volume, and more than 100 mg/L anthocyanin.

2. The method of claim 1, further comprising adding an appropriate amount of solid red bayberry residues to said red bayberry juice during said aerobic fermentation process.

3. The method of claim 2, wherein said appropriate amount of solid red bayberry residues is 20-140 g/L red bayberry juice.

4. The method of claim 1, wherein the culture broth obtained from said aerobic fermentation and said anaerobic fermentation is filtered and further incubated at 4-8° C. for 20-30 days.

5. The method of claim 1, comprising the steps of:
   a). providing a squeezed, filtered and sterilized red bayberry juice;
   b). performing a primary fermentation which comprises incubating said red bayberry juice with *Pichia kluyveri* XT110, wherein said primary fermentation comprises said aerobic fermentation followed by said anaerobic fermentation;
   c). performing a secondary fermentation which comprises filtering culture broth obtained from step b) and incubating said filtered culture broth at 4-8° C. for 20-30 days; and
   d). adjusting sugar content and acidity of said culture broth obtained from step c), and sterilizing said adjusted culture broth to obtain said fermented nonalcoholic red bayberry beverage.

6. The method of claim 5, wherein 20-140 g solid red bayberry residue per liter of red bayberry juice is added during said aerobic fermentation in step b).

7. The method of claim 6, wherein 80 g said solid red bayberry residue per liter of red bayberry juice is added during said aerobic fermentation.

8. The method of claim 5, wherein said aerobic fermentation is performed at 28° C. for 4 hours and said anaerobic fermentation is performed at 28° C. until achieving a weight loss of 2.3±0.2 g/L fermentation medium.

9. The method of claim 1, ripe, undecayed, deep-colored red bayberries are used as starting materials.

10. The method of claim 1, wherein said fermented nonalcoholic red bayberry beverage has a sensory score higher than 78.

* * * * *

SEQUENCE LISTING

<160> NUMBER OF SEQ ID NOS: 1

<210> SEQ ID NO 1
<211> LENGTH: 578
<212> TYPE: DNA
<213> ORGANISM: Pichia kluyveri

<400> SEQUENCE: 1

-continued

```
gaggaaaagg aaaccaacag ggattgcctc agtagcggcg agtgaagcgg caagagctca      60
gatttgaaat ctcacctagt gtgcgagttg taaattgcag gttggagtct cgggttagac     120
gtgtgtgcaa gtcccttgga acagggtgcc actgagggtg agagcccgt agcgtgcatg     180 tcgacacctg tgaggccctt ctgacgagtc gagttgtttg ggaatgcagc tctaagtggg     240
tggtaaattc catctaaggc taaatattgg cgagagaccg atagcgaaca agtactgtga     300
aggaaagatg aaaagcactt tgaaaagaga gtgaaacagc acgtgaaatt gttgaaaggg     360
aagggtattg ggctcgacat gggatttacg catcgttgcc tctcgtgggc ggcgctctgg     420 gttttttcctg ggccagcatc ggttttcgtt gcaggataag gacaattgga atgtggctcc    480
tcggagtgtt atagccttt gtagatgctg cgtatgggga ccgagggctg cggcggactc      540
gtttcgtctc ggatgctggc acaacggcgc aataccgc                             578
```